Figure 1:
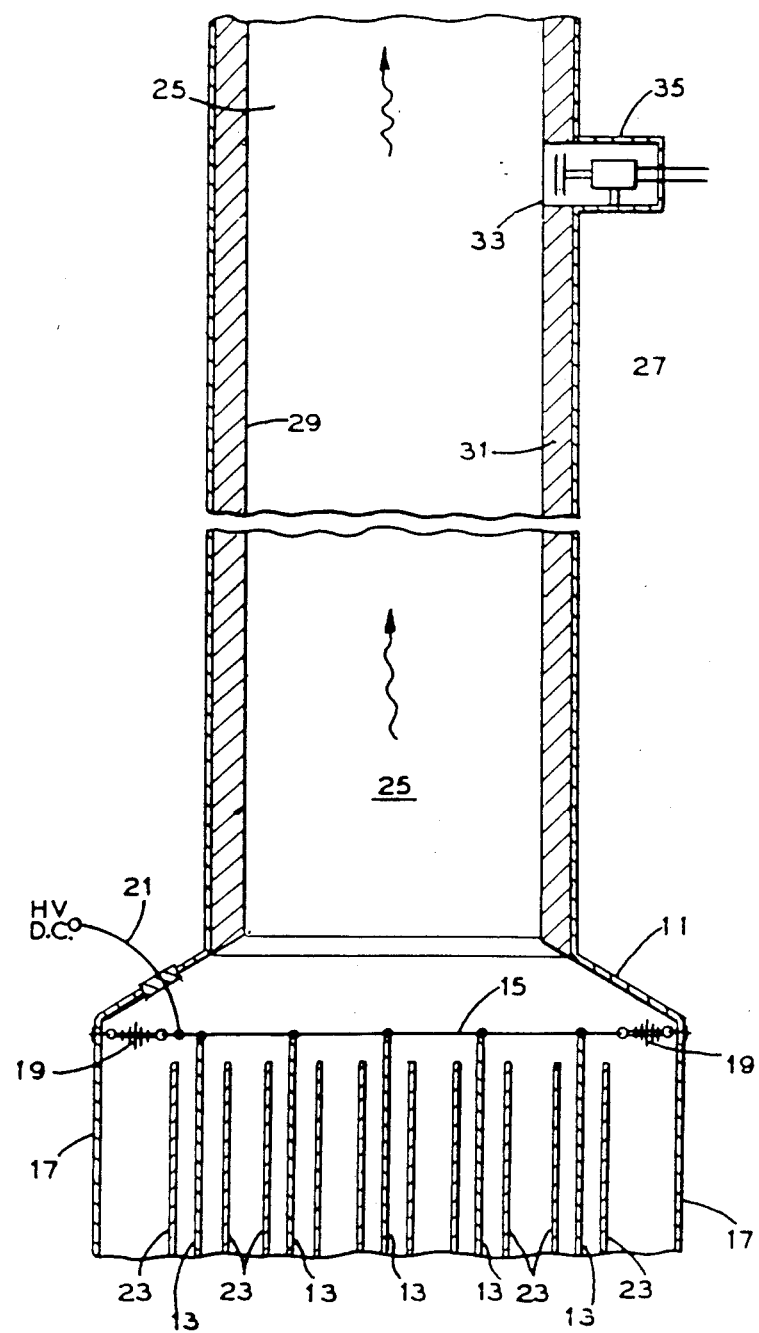

United States Patent [19]

Castle et al.

[11] Patent Number: 4,973,909
[45] Date of Patent: Nov. 27, 1990

[54] SYSTEM FOR THE MEASUREMENT OF THE CONCENTRATION PARTICULATES IN A FLOWING GAS

[75] Inventors: G. S. Peter Castle; Ion I. Inculet, both of London, Canada; Stig Lundquist, Knivsta, Sweden; William J. Middleton, Sudbury, Canada

[73] Assignees: University of Western Ontario, London; Inco Limited, Toronto, both of Canada

[21] Appl. No.: 466,585

[22] Filed: Jan. 17, 1990

Related U.S. Application Data

[63] Continuation of Ser. No. 245,044, Sep. 16, 1988, abandoned.

[51] Int. Cl.⁵ .................. G01N 27/60; G01R 29/12
[52] U.S. Cl. ............................ 324/452; 324/457; 55/104
[58] Field of Search ............. 324/452, 454, 455, 457, 324/458, 464, 71.1, 71.4, 72; 73/23, 28; 55/103–105

[56] References Cited

U.S. PATENT DOCUMENTS 4,556,849  12/1985  Kalakutsky et al. ............... 324/464

FOREIGN PATENT DOCUMENTS 0004124  9/1979  European Pat. Off. ............ 324/464

OTHER PUBLICATIONS

Abramyan et al, Devices for Monitoring Static Electricity in Particle-Bearing Gas Flows, 5-1978, pp. 702–704.

Primary Examiner—Gerard R. Strecker
Assistant Examiner—Jack B. Harvey
Attorney, Agent, or Firm—Francis J. Mulligan, Jr.; Edward A. Steen

[57] ABSTRACT

A system for estimating the burden of particulate levitated in a flow of gas which includes an upstream device for electrically charging the particulate, a downstream device for sensing the intensity of the field produced by the electrically charged particulate and an indicating device sensitive to an output of the downstream sensing device.

8 Claims, 2 Drawing Sheets

SYSTEM FOR THE MEASUREMENT OF THE CONCENTRATION PARTICULATES IN A FLOWING GAS

This is a continuation of copending application Ser. No. 07/245,044 filed on 9/16/88 now abandoned.

The present invention is concerned with measurement of the concentration of particulates in a gas stream and, more particularly, with the measurement of the concentration of particulates in a flowing gas downstream of a Cottrell TM-type precipitator.

BACKGROUND OF THE INVENTION AND PROBLEM

The measurement of particulates carried along in a gas stream, e.g. in a smoke stack, is sometimes difficult. Interference with or diminution in intensity of a light beam is one method which is commonly practiced. Generally speaking, such a system includes a light source, a photodetector and means to calibrate lowering of the output of the photodetector with the particulate burden of the gas flowing between the source and the detector. Some difficulties may be encountered with such a system. Firstly, at best, the system will measure particulate concentration only in the path of the light beam which usually is only a minute fraction of the cross-sectional area of the gas duct or flue carrying the particulate. Secondly, surfaces on both the light source and the detector are likely to get dirty rather quickly leading to error in calibration of the system and the need for frequent cleaning. As a third point, condensate in a chimney or flue such as microscopic and submicroscopic water or sulfuric acid particles can scatter the light beam and thus indicate a particulate load, i.e. a solid particulate burden greater than what actually exists. As an additional point, a light beam detector may be overwhelmed by the amount and/or the color of levitated particles and, once the gas stream becomes opaque to the light, no additional particulate can be detected. Finally, especially in stacks, flues and chimneys carrying off-gases from sulfide oxidation, light beam source and detector parts are subject to significant corrosion in use.

Another system often used for estimation of the particulate burden of a gas flow comprises essentially particulate entrapment by filtering, impactment and capture or the like. This type of system can be very accurate but usually cannot be operated in a sufficiently timely fashion so as to provide data useful for control of a collection device such as a Cottrell TM precipitator.

OBJECTS AND DESCRIPTION OF THE INVENTION

It is an object of the present invention to provide a system for quantitatively estimating the amount of particulate levitated in a gas by electrostatic means.

It is a further object of the invention to provide a system in which particulate levitated in a flowing gas is electrostatically charged by corona, a major portion of said particulate is precipitated on a grounded surface or surface and the remainder of said particulate levitated in the flowing gas is quantitatively estimated.

In its preferred aspect the invention comprises a system for quantitatively estimating the amount of particulate levitated in a gaseous fluid escaping a corona-charging precipitating device which includes in combination: a corona-charging device adapted to electrically charge particulate levitated in a gaseous fluid; means to precipitate a significant portion of said particulate; a flue downstream of said corona-charging device adapted to carry the whole or a representative part of said gaseous fluid plus particulate escaping said corona-charging device; means at a wall of said flue to sense the intensity of the electric field within said flue; and means responsive to said sensing means to indicate the intensity of the electric field in said flue calibrated to discount the background electric field due to entrainment of ions and ion clusters by said gaseous fluid and to indicate the particulate load of said gaseous fluid by the intensity of said electrical field in excess of said background electrical field.

In a somewhat broader aspect of the invention the burden or concentration of particulate levitated in a flowing gas is determined by artificially inducing on said particulate or a predetermined portion of said particulate an electric charge at a first site along the flow path of the gas, providing means at a wall of said flow path spaced apart from said first site to sense the intensity of the electric field within said flow path and providing means responsive to said sensing means to indicate the intensity of the electric field in said flow path calibrated to discount the background electric field due to entrainment of ions and ion clusters by said gas and to indicate the particulate load of said gaseous fluid by the intensity of said electrical field in excess of said background electrical field.

Those skilled in the art will appreciate that the two aforestated aspects of the invention differ principally in that the more restricted, first stated aspect, is specifically concerned with measurements which will indicate the efficiency of an electrostatic precipitator. The second aspect provides a means or system for monitoring the flow of solid in a gas independent of any collection or precipitation device. Accordingly, in the broader aspect, charging of particulate in a flowing gas stream is not limited to corona charging but may also be accomplished by any charging means capable of substantially uniformly charging gas levitated particulate. For example, charging can be accomplished by radiation, electron gun induction, triboelectrification or by evaporating charged water droplets as well as by corona devices.

DRAWINGS

FIG. 1 of the drawing is a schematic representation of a system involving an electrostatic precipitator and a gas flue exiting therefrom.

Figure 2:
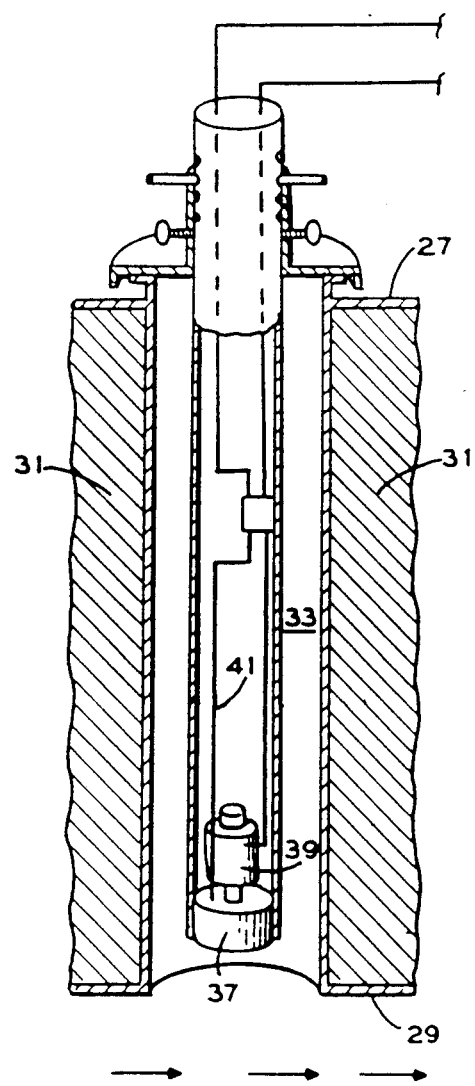

FIG. 2 is a depiction of an electric field meter adapted to be employed in the wall of the flue of FIG. 1.

SPECIFIC DESCRIPTION OF THE INVENTION

Even the best electrostatic precipitators are not 100% efficient with respect to the collection of particles passing through them. It is well known that these untrapped particles can possess considerable charge and as such these particles generate space charges. The space charge density $\rho(\mu C/m^3)$ in the flues downstream of the electrostatic precipitator is a function of the charge-to-mass ratio of the aerosols, $q(\mu C/g)$, and the particle concentration in the gas, $d(g/m^3)$, i.e.

$$\rho = q\,d$$

The value of the electric field established between the charged aerosol particles and the grounded flue surface has been calculated for both cylindrical and rectangular ducts. At a point in space, the electric field, E(V/m), is a direct function of the space charge density and the volume of the aerosol $$E \propto \int \rho \cdot dv$$

where dv is an elementary volume.

For electrostatic precipitators treating aerosols of relatively uniform size distribution and chemical composition and exhibiting stable electrical operation, the charge-to-mass ratio of the uncaptured particles will be essentially constant. At a fixed point the electric field will then be a direct function of the aerosol concentration in the gas stream. The electric field reading should then give an indirect measurement or indication of mass emission rate.

A particularly useful means to sense the intensity of the electric field of a flowing gas stream is an electric field mill wherein an electric motor is employed to drive a rotating "shutter" to modulate the charge induced on sensing electrodes. The electric field meter used in establishing utility of the present invention in exhaust gas systems of a metallurgical operation fed with sulfide mineral was specially designed to have: (a) the capability to operate continuously and reliably at temperatures between 50° and 350° C. and in corrosive atmospheres frequently containing both condensed moisture and sulfuric acid; (b) simplicity of operation and ease of maintenance; and (c) a measuring range up to 1500 V/cm based on preliminary electric field measurements.

Establishing operability of the system of the present invention was done in equipment as schematically depicted in the drawing. Referring now thereto, and especially to FIG. 1, gas flows out of electrostatic precipitator 11 upwardly. During residence in electrostatic precipitator 11, it is subject to the influence of corona wires 13 fixed to hanger 15 which in turn is isolated from walls 17 by insulators 19. Hanger 15 is connected to a high voltage direct current source (not illustrated) through lead 21. Electrostatic precipitator 11 also includes grounded surfaces 23 which can be of any configuration, e.g. plates, tubes, etc. In operation as dust laden gas passes through electrostatic precipitator 11, the dust particles are charged in the fields surrounding corona wires 13 and then for the most part are deposited on grounded surfaces 23. Gas, along with charged dust particles, enters flue 25. Flue 25 comprises outer wall 27 and inner wall 29 and can be of any customary cross-sectional shape. Between walls 27 and 29 is a layer of heat insulation 31. At a convenient site in flue 25 downstream of electrostatic precipitator 11, a port 33 is made to permit insertion of electric field mill 35. Electric field mill 35 is shown in greater detail in FIG. 2. Referring now thereto, sensing head 37 of electric field mill 35 is mounted in port 33 very close to inner wall 29 of flue 25. Sensing head 37 consists of insulated electrodes and rotating shutter (not depicted). As is conventional, the electrodes are mounted so as to be insulated from grounded flue walls 27 and 29 and to face the interior of flue 25 when exposed through holes in the rotating shutter. The electrodes thus couple with the electrostatic field in flue 25 intermittently because of the shutter action. The shutter is rotated at a substantially constant speed by motor 39, e.g. an electric motor. An electric signal from electrodes in sensing head 37 passes through line 41 to a conventional amplifier, recorder and optional feedback control mechanisms controlling electrostatic precipitator 11. It is deliberately arranged so that electric field mill 35 does not totally block port 33. In this way the natural draft in a chimney or flue 25 will cause a flow of clean air from the exterior into flue 25 through port 33 thereby cooling electric field mill 35 and substantially isolating it from a corrosive atmosphere in flue 25. Even with such an arrangement it may be necessary to provide additional air flow, for example, by means of a fan operating off motor 39. As a precaution, metal parts of, and associated with, electric field mill 35 should be made of corrosion resistant metal such as austenitic stainless steel.

In operation, the periodic blocking of the field inside flue 25 by the rotating shutter produces an AC signal from the electrodes that is proportional to the incident electric field strength. The electrical design of electric field meter 35 is such that a 0-1 V DC output signal corresponds linearly (within 1%) to a 0-1000 V/cm electric field strength. The output signal can be read on a meter, chart recorder, or modified for input to a computer. When operated at a nominal 3600 rpm, a 25% change in rotational speed of the shutter produces less than a 1% change in the output signal. Two shutter drive systems were designed for electric field meter 35. The initial prototype used a commercial air tool turbine designed to operate at 1900 rpm when driven by air at 414 kPa pressure. Exhaust air also served to purge the electrodes and insulators with clean air. During field testing, however, difficulty was experienced with supplying clean high pressure air to the unit which led to frequent seizing of the turbine. The mechanical drive system was then abandoned in favor of an electrical drive motor 39.

During testing, sensing head 37 of electric field meter 35 was recessed about 5 cm from the inner flue surface 29. This was required to keep sensing head 37 of electric field meter 35 clean. While some distortion of the electric field was experienced, it was not sufficient to affect either detection of variations in field strength due to changes in precipitator operation or electric field-mass emission correlations. Specific test objectives were:

1. to determine the response of electric field meter 35 output to changes in electrostatic precipitator operation (i.e. rapping, etc.) and process activity (i.e. variable inlet mass loadings);

2. to determine the suitability of electric field meter 35 for the continuous measurement of mass emissions; and 3. to assess the performance of electric field meter 35 in terms of reliability and accuracy.

Field tests were conducted in the following manner. Electric field meter (or mill) 35 was installed in a port 33 in the wall of a 381 meter tall stack which is fed by a complex flue system. The stack receives and disperses gases resulting from various metallurgical operations such as converting in Peirce-Smith converters, converting in top-blown rotary converters (TBRC's), roasting in quiescent roasters, roasting in fluid bed roasters and smelting in reverberatory furnaces. Prior to being received into the stack, the gases are passed through any one or more of six electrostatic precipitators 11 to remove the greater part of particulate burden from them. Various activities of the metallurgical operations and electrostatic precipitators 11 were monitored. Prior to each test, the electric field meter 35 output was zeroed on a chart recorder by aiming the field meter at a grounded surface. Electric field meter 35 was then positioned in access port 33 as described. The electric field meter 35 output signal was continuously recorded throughout the test (usually 1-4 hours duration depending on the activity being monitored) and the average field strength was calculated for the period.

Mass emissions were measured independently using the standard ASTM sampling technique as described in Bulletin WP-50, 7th Edition, Western Precipitation Division, Joy Manufacturing Company. An appropriately sized sampling tip connected to an in-stack filter was positioned in flue 25 at the average velocity point. Gas sampling rates were adjusted as required to maintain isokinetic conditions. The sample filter and contents were dried at the conclusion of each test prior to weighing. Filter contents were analyzed for condensed sulfuric acid, hydrolyzed moisture, and selected elements. Testing was conducted to cover the expected range of emissions characteristic for each electrostatic precipitator system.

The output voltage of electric field meter 35 was monitored during blowing-not blowing cycles of Peirce-Smith converters. Uniformly it was found that during blowing a meter reading of about 210 mV was observed. However, when no blowing occurred the meter reading dropped precipitously to about 25 mV. When electrostatically precipitated dust was being pneumatically transferred in the duct system (shooting) a meter reading of about 50 mV was observed in contrast to a meter reading of about 40 mV characteristic of "normal" operation. Rapping of electrostatic precipitator 11, i.e. releasing precipitated dust by mechanical force, resulted in meter readings of roughly 150 mV as opposed to readings of about 100 mV characteristic of "normal" operation. When observing electrostatic fields existing in nickel converter gases treated by electrostatic precipitation, it was found that there is a reasonably linear relationship between particulate mass emission rate expressed in tonnes/day and the meter reading in millivolts. In the stack used in testing a mass emission rate of about 0.25 tonnes/day equated to a meter reading of about 0.60 mV and a mass emission rate of about 1.25 tonnes/day equated to a meter reading of about 270 mV. When observing electrostatic fields existing in gases arising out of reverberatory furnaces after electrostatic precipitation treatment, again a reasonably linear correlation existed between particulate mass emission rate and meter reading. A meter reading of about 90 mV equated to zero mass emission rate and a meter reading of about 150 mV equated to a mass emission rate of about 4 tonnes/day. No observable relationship was found between mass emission rate and meter reading as to multi-hearth roaster gases treated by electrostatic precipitation.

When the present invention is employed to measure the particulate burden of a gas flow in the absence of electrostatic precipitation, the particulates on the whole or a known representative (aliquot) portion of the gas flow are charged, as for example by means of charging system such as used in the ionizing stage of a two-stage electrostatic precipitator. In such a system, it is required that a standard charge be applied to the gas levitated particulate. Accordingly, it is recommended because of the difficulty of producing consistent fractional charges that the charging device be designed such that the particulate is charged to the practical limiting value of:

$$Q_o = AE_o a^2$$

(where $Q_o$ = limit value of charge, A is a constant depending upon the electrical conductivity of the particulate, $E_o$ is the intensity of the electrical field and a is the average particle radius greater than about one micrometer) as reported by Pauthenier & Moreau-Hanot, The Electrician, Aug. 10, 1934, pages 187 et seq. Measurement of the field produced by such charged particles downstream of the charging station will then give a measurement of the concentration of particles in the flowing gas stream. Charging particulate to the limiting value can also be used to aid in calibration of systems measuring particulate escaping from electrostatic precipitator.

While in accordance with the provisions of the statute, there is illustrated and described herein specific embodiments of the invention, those skilled in the art will understand that changes may be made in the form of the invention covered by the claims and that certain features of the invention may sometimes be used to advantage without a corresponding use of the other features.

We claim:

1. A continuously operative system for determining the concentration of particulate levitated in a flowing stream of gas consisting of:
    (a) upstream means to induce an electric charge on at least a portion of said levitated particulate;
    (b) downstream means to sense the intensity of the electric field produced by said levitated particulate electrically charged by said upstream means and flowing past said downstream means; and
    (c) means responsive to said downstream means to indicate the intensity of said electric field calibrated to discount any background electric field and to indicate the concentration of said levitated particulate by the intensity of said electric field in excess of any background electric field.

2. A system as in claim 1 wherein said upstream means is an electrostatic precipitator.

3. A system as in claim 1 wherein said upstream means is adapted to induce an electric charge on an aliquot of said particulate.

4. A system as in claim 1 wherein said means to induce an electric charge is a corona charging device.

5. A system as in claim 4 wherein said corona charging device is a part of an electrostatic precipitator.

6. A system as in claim 1 wherein said downstream means is an electric field mill.

7. A system as in claim 6 wherein said electric field mill includes a rotating shutter driven by an electric motor.

8. A system as in claim 6 wherein said electric field mill is mounted in a wall of a flue guiding said flowing stream of gas and is cooled by ambient air flowing past said electric field mill and into said flue.

* * * * *